United States Patent [19]

Hoffmann et al.

[11] 4,307,033
[45] Dec. 22, 1981

[54] PREPARATION OF 3,3-DIMETHYL-CYCLOPROPANE-1,1,2-TRICARBOXYLIC ACID DERIVATIVES AND INTERMEDIATES THEREFOR

[75] Inventors: Hellmut Hoffmann; Fritz Maurer, both of Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 153,288

[22] Filed: May 27, 1980

[30] Foreign Application Priority Data

Jun. 12, 1979 [DE] Fed. Rep. of Germany ....... 2923778

[51] Int. Cl.$^3$ .................. C07C 120/00; C07C 121/46; C07C 121/16; C07C 121/30
[52] U.S. Cl. .................................... 260/464; 560/124; 562/506; 260/465.7
[58] Field of Search ......................................... 260/464

[56] References Cited

U.S. PATENT DOCUMENTS

| | | | |
|---|---|---|---|
| 4,118,412 | 10/1978 | Cleare et al. | 260/464 |
| 4,195,033 | 3/1980 | Punja | 260/464 |
| 4,198,347 | 4/1980 | Punja | 260/464 |

FOREIGN PATENT DOCUMENTS

| | | |
|---|---|---|
| 965580 | 5/1957 | Fed. Rep. of Germany . |
| 1108214 | 6/1961 | Fed. Rep. of Germany ...... 260/464 |
| 2621830 | 11/1976 | Fed. Rep. of Germany . |
| 2724734 | 12/1977 | Fed. Rep. of Germany . |
| 2730755 | 1/1978 | Fed. Rep. of Germany . |
| 2926852 | 2/1980 | Fed. Rep. of Germany . |

OTHER PUBLICATIONS

Verhe, et al.; Bull. Soc. Chim. Belg., 86 (1977), pp. 55–63.
Kristensen, et al.; Bull. Soc. Chim. Belg., 87 (1978), pp. 721–732.
Ghosh, J. of Ind. Chem. Soc., 14 (1937), pp. 449–451.
McElvain, et al., J. A. C. S., 81 (1959), pp. 2579–2588.
Owen, et al., J. of Chem. Soc. (London), 1949, pp. 3089–3098.
Hargreaves, et al., J. of Chem. Soc. (London), 1947, pp. 750–752.
Murfitt, et al., J. of Chem. Soc. (London), 1944, pp. 371–373.
Hart, et al., J. A. C. S., 85 (1963), pp. 1161–1185.

C. A., 53 (1959), 10075c, Bayer.

*Primary Examiner*—Joseph Paul Brust
*Attorney, Agent, or Firm*—Sprung, Felfe, Horn, Lynch & Kramer

[57] ABSTRACT

3,3-Dimethyl-cyclopropane-1,1,2-tricarboxylic acid derivatives of the formula

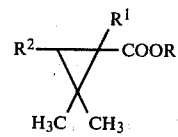

in which
R is alkyl, and
$R^1$ and $R^2$ each is alkoxycarbonyl or cyano, with the proviso that at least one of them is cyano, suitable for use as intermediates in making insecticides, are produced by reacting a $\beta,\beta$-dimethyl-acrylic acid nitrile of the formula

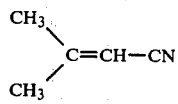

with bromine or chlorine at a temperature between about $-20°$ and $+50°$ C. to produce a compound of the formula

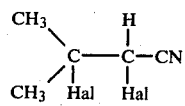

in which
Hal is chlorine or bromine, which compound is further reacted with a malonic acid derivative of the formula

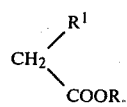

7 Claims, No Drawings

PREPARATION OF 3,3-DIMETHYL-CYCLOPROPANE-1,1,2-TRICARBOXYLIC ACID DERIVATIVES AND INTERMEDIATES THEREFOR

The invention relates to an unobvious process for the preparation of certain known 3,3-dimethyl-cyclopropane-1,1,2-tricarboxylic acid derivatives, and to α-halogenonitriles as new intermediate products for this process, and to processes for their preparation.

It is known that 3,3-dimethyl-cyclopropane-1,1,2-tricarboxylic acid triethyl ester is obtained when α,β-dibromo-β,β-dimethyl-propionic acid ethyl ester is reacted with malonic acid diethyl ester in the presence of sodium ethylate (see J. Indian Chem. Soc. 14 (1937), 449–451).

However, in this reaction, about two parts of 3-methyl-but-2-ene-1,1,2-tricarboxylic acid triethyl ester and about three parts of 3-methyl-but-3-ene-1,1,2-tricarboxylic acid triethyl ester are in general obtained per part of 3,3-dimethyl-cyclopropane-1,1,2-tricarboxylic acid triethyl ester; the desired product is thus obtained only as a by-product.

It is also known that 3,3-dimethyl-cyclopropane-1,1,2-tricarboxylic acid derivatives, for example 3,3-dimethyl-cyclopropane-1,1,2-tricarboxylic acid triethyl ester or 3,3-dimethyl-cyano-cyclopropane-1,2-dicarboxylic acid diethyl ester, are obtained when isopropylidenemalonic acid diethyl ester or, respectively, isopropylidene-cyanoacetic acid ethyl ester is reacted with dimethylsulphuranylidene-acetic acid ethyl ester in aprotic solvents (see J. Org. Chem. 32 (1967), 3,351–3,355). However, because of the sensitivity of dimethylsulphuranylidene-acetic acid ethyl ester to moisture, the reactions for the preparation and conversion of this compound must be carried out in thoroughly dried media. In addition, dimethylsulphuranylidene-acetic acid ethyl ester must be stored at a low temperature, since it gradually decomposes at normal temperature.

It is furthermore known that 3,3-dimethyl-2-cyanocyclopropane-1,1-dicarboxylic acid dimethyl ester or diethyl ester is obtained when (2-bromo-2-methylpropylidene)-malonic acid dimethyl ester or diethyl ester is reacted with sodium cyanide or potassium cyanide (see Bull. Soc. Chim. Belg. 86 (1977), 55–63; and ibid. 87 (1978), 721–732). The synthesis given in the literature for the (2-bromo-2-methylpropylidene)-malonic acid esters, to be used as starting materials, by reaction of (2-methyl-propylidene)-malonic acid esters with N-bromosuccinimide is, however, not very suitable for preparation on a large industrial scale.

The present invention now provides:

(1) a process for the preparation of a 3,3-dimethylcyclopropane-1,1,2-tricarboxylic acid derivative of the general formula $$R^2 - \underset{H_3C \quad CH_3}{\overset{R^1}{\diagup}} - COOR \qquad (I)$$

in which
R represents alkyl and
$R^1$ and $R^2$ represent alkoxycarbonyl or cyano, with the proviso that at least one of these radicals represents cyano, characterized in that an α-halogenocarboxylic acid derivative of the general formula $$\underset{CH_3}{\overset{CH_3}{\diagdown}} C_\beta - \underset{R^3}{\overset{R^5}{\underset{|}{C_\alpha}}} - R^2, \qquad (II)$$

in which
$R^2$ represents alkoxycarbonyl or cyano,
$R^3$ represents bromine or chlorine,
$R^4$ represents hydrogen, or, together with $R^5$, an additional bond between $C_\alpha$ and $C_\beta$, and
$R^5$ represents bromine or chlorine, or, together with $R^4$, an additional bond between $C_\alpha$ and $C_\beta$, is reacted with a malonic acid derivative of the general formula $$CH_2 \underset{COOR}{\overset{R^1}{\diagup}} \qquad (III)$$

in which
R and $R^1$ have the meanings indicated above, if appropriate in the presence of a base and if appropriate using a diluent, at a temperature between 0° and 100° C.;

(2), as new compounds, the α-halogeno-nitriles of the general formula $$\underset{CH_3}{\overset{CH_3}{\diagdown}} C_\beta - \underset{R^3}{\overset{R^5}{\underset{|}{C_\alpha}}} - CN, \qquad (IIa)$$

in which
$R^3$ represents bromine or chlorine,
$R^4$ represents hydrogen, or, together with $R^5$, an additional bond between $C_\alpha$ and $C_\beta$, and
$R^5$ represents bromine or chlorine, or, together with $R^4$, an additional bond between $C_\alpha$ and $C_\beta$;

and (3) a process for the preparation of an α-halogenonitrile of the formula (IIa) above, characterized in that β,β-dimethyl-acrylic acid nitrile, of the formula $$\underset{CH_3}{\overset{CH_3}{\diagdown}} C = CH - CN, \qquad (IV)$$

is reacted with bromine or chlorine, if appropriate in the presence of a diluent, at a temperature between −20° and +50° C., and the halogenation product of the formula (IIa) ($R^4$=H and $R^5$=Cl or Br) is optionally treated with a base at a temperature between 0° and 100° C. in order to eliminate hydrogen halide.

Surprisingly, 3,3-dimethyl-cyclopropane-1,1,2-tricarboxylic acid derivatives of the formula (I) can be prepared in good yields and in high purity in a considerably more simple and less expensive manner by process (1) according to the invention than by known methods.

The new process is thus very suitable for the industrial preparation of 3,3-dimethyl-cyclopropane-1,1,2-tricarboxylic acid derivatives.

If, for example, α,β-dichloro-iso-valeric acid methyl ester and cyanoacetic acid ethyl ester are used as starting compounds, the course of the reaction in process (1) can be outlined by the following equation:

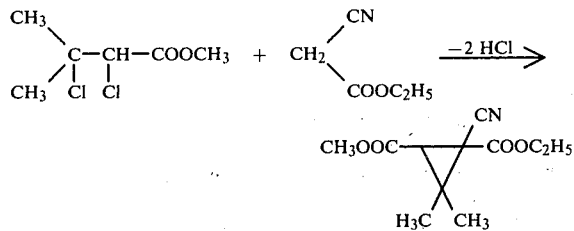

Formula (II) provides a definition of the α-halogenocarboxylic acid derivatives to be used as starting compounds in process (1). Preferably, in this formula, $R^2$ represents $C_1$–$C_4$-alkoxy-carbonyl or cyano, $R^3$ represents bromine or chlorine, $R^4$ represents hydrogen, or, together with $R^5$, an additional bond between $C_\alpha$ and $C_\beta$, and $R^5$ represents bromine or chlorine, or, together with $R^4$, an additional bond between $C_\alpha$ and $C_\beta$.

Examples of the compounds (II) which may be mentioned are: α,β-dibromo-iso-valeric acid methyl ester, ethyl ester, n-propyl ester, iso-propyl ester, n-butyl ester, iso-butyl ester, sec.-butyl ester and tert.-butyl ester, α,β-dichloro-iso-valeric acid methyl ester, ethyl ester, n-propyl ester, iso-propyl ester, n-butyl ester, iso-butyl ester, sec.-butyl ester and tert.-butyl ester, α-bromo-β,β-dimethyl-acrylic acid methyl ester, ethyl ester, n-propyl ester, iso-propyl ester, n-butyl ester, iso-butyl ester, sec.-butyl ester and tert.-butyl ester, α-chloro-β,β-dimethyl-acrylic acid methyl ester, ethyl ester, n-propyl ester, iso-propyl ester, n-butyl ester, iso-butyl ester, sec.-butyl ester and tert.-butyl ester, α,β-dibromo-isovaleric acid nitrile, α,β-dichloro-iso-valeric acid nitrile, α-bromo-β,β-dimethyl-acrylic acid nitrile and α-chloro-β,β-dimethyl-acrylic acid nitrile.

Compounds of the formula (II) in which $R^2$ represents alkoxycarbonyl are known (see J. Chem. Soc. (London) 1944, 371–373; ibid. 1947, 750–752; ibid. 1949, 3,089–3,098; and J. Am. Chem. Soc. 81 (1959), 2,579–2,588).

Compounds of the formula (II), in particular the new compounds of the formula (IIa), are obtained by the process described above, under (3), by reacting β,β-dimethyl-acrylic acid derivatives, in particular β,β-dimethyl-acrylic acid nitrile of the formula (IV), with bromine or chlorine, if appropriate in the presence of a diluent, for example carbon tetrachloride, at a temperature between −20° and +50° C., preferably between 0° and 40° C., and then optionally reacting the halogenation product with a base, for example potassium carbonate, if appropriate using a diluent, for example dimethylformamide, at a temperature between 0° and 100° C., preferably between 10° and 80° C.

The mixture can be worked up by customary methods, for example by diluting with ether, washing with water, drying and filtering and, if appropriate, subjecting the product phase to vacuum distillation.

The β,β-dimethyl-acrylic acid nitrile (IV) to be employed as the starting compound in the process described under (3) for the preparation of new α-halogenonitriles of the formula (IIa) is already known (see U.S. Pat. No. 2,500,403).

Formula (III) provides a definition of the malonic acid derivatives also to be used as starting substances in process (1). Preferably, in this formula:

R represents $C_1$–$C_4$-alkyl and $R^1$ represents $C_1$–$C_4$-alkoxy-carbonyl or cyano.

Examples which may be mentioned are: malonic acid dimethyl ester, diethyl ester and dipropyl ester and cyanoacetic acid methyl ester, ethyl ester, n-propyl ester, iso-propyl ester, n-butyl ester, iso-butyl ester, sec.-butyl ester and tert.-butyl ester.

The malonic acid derivatives of the formula (III) are known compounds.

Process (1) is preferably carried out using a diluent. Preferred diluents are polar organic solvents. These include carboxylic acid amides, for example dimethylformamide and N-methylpyrrolidone; sulphoxides and sulphones, for example dimethylsulphoxide and tetramethylene sulphone; phosphoric acid amides, for example hexamethylphosphoric acid triamide; ethers, for example glycol dimethyl ether, diglycol dimethyl ether, tetrahydrofuran and dioxane; nitriles, for example acetonitrile and propionitrile; and alcohols, for example methanol, ethanol, n- and iso-propanol and n-, iso-, sec.- and tert.-butanol.

Any of the customary acid-binding agents can be used as the base. Acid-binding agents which have proved particularly suitable are alkali metal carbonates and alcoholates, such as sodium carbonate and potassium carbonate and sodium methylate and ethylate and potassium methylate and ethylate, and furthermore aliphatic, aromatic or heterocyclic amines, for example triethylamine, trimethylamine, dimethylaniline, dimethylbenzylamine, pyridine and diazabicyclononane.

The reaction temperature can be varied within a substantial range. In general, the reaction is carried out between 0° and 100° C., preferably at from 10° to 80° C.

The process according to the invention is in general carried out under normal pressure.

1 to 3 mols, preferably 1 to 2 mols, of malonic acid derivative of the formula (III) are in general employed per mol. of α-halogeno-carboxylic acid derivative of the formula (II).

In a preferred embodiment of process (1), the malonic acid derivative (III) is initially introduced with about an equimolar amount of one of the above-mentioned bases in one of the above-mentioned diluents, and an α-halogeno-carboxylic acid derivative (II) is added dropwise to this mixture, while stirring. The entire reaction mixture is stirred at a temperature between 40° and 80° C. for several hours. Working up is effected in the customary manner: after stripping off the solvent in vacuo, water and a water-immiscible solvent, for example ether, are added to the residue and the mixture is shaken. The organic phase is separated off, dried and filtered and the filtrate is concentrated. The crude product which remains can be purified by vacuum distillation. The boiling point is used for its characterization.

The 3,3-dimethyl-cyclopropane-1,1,2-tricarboxylic acid derivatives to be prepared by process (1) can be converted into 3,3-dimethyl-cyclopropane-1,2-dicarboxylic acid (caronic acid) by partial hydrolysis, decarboxylation and further hydrolysis, according to the following equation ($R^1$, $R^2$=CN, COOalkyl):

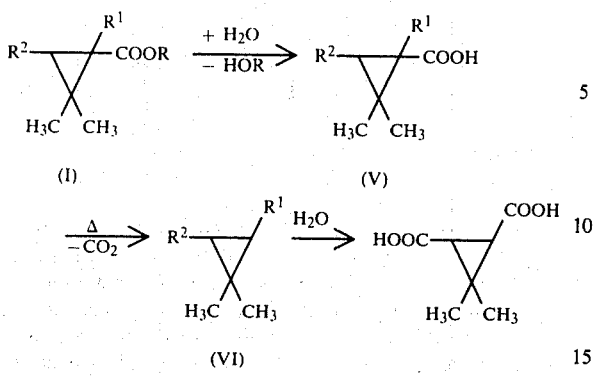

For this conversion, a 3,3-dimethyl-cyclopropane-1,1,2-tricarboxylic acid derivative (I) is first reacted with a base, for example sodium hydroxide or potassium hydroxide, if appropriate using a diluent, for example methanol or water, at a temperature between 0° and 80° C., preferably between 10° and 50° C. To isolate the compound of the formula (V) thereby formed, the mixture is acidified, the oily product which thereby separates out is taken up in methylene chloride, the solution is dried and filtered and the filtrate is concentrated. The crude product which remains can be used for the next stage without further purification.

For the decarboxylation, the carboxylic acid of the formula (V) is heated to a temperature between 120° and 200° C., if appropriate in the presence of a diluent, for example dimethylformamide or dimethylsulphoxide. Working up and isolation of the compound of the formula (VI) thereby formed is carried out by customary methods: the mixture is poured into water and extracted with a water-immiscible organic solvent, such as, for example, methylene chloride, the extracts are dried and concentrated and, if appropriate, the product is purified by vacuum distillation.

Partial hydrolysis and decarboxylation can also be combined, by heating a compound of the formula (I) to a temperature between 100° and 250° C., preferably between 120° and 200° C., with an approximately equimolar amount of water in a high-boiling organic solvent, for example dimethylformamide or dimethylsulphoxide. In order to work up and isolate the product of the formula (VI) thereby formed, the mixture is diluted with a water-immiscible solvent (for example with toluene), washed with water, dried and concentrated and, if appropriate, the product is distilled under reduced pressure.

Compounds of the formula (VI) can be converted into 3,3-dimethyl-cyclopropane-1,2-dicarboxylic acid (caronic acid) by hydrolysis, for example by heating to a temperature between 80° and 120° C. with an alkali metal hydroxide solution, for example 15% strength sodium hydroxide solution, and then acidifying the mixture at room temperature with a strong acid, for example hydrochloric acid. Caronic acid is thereby obtained as crystals and can be isolated by filtration.

Caronic acid or esters thereof can be used as intermediate products for the preparation of insecticidally and acaricidally active pyrethroids (compare Pestic. Sci. 7 (1976), 492-498; and Tetrahedron Lett. 1978, 1,847-1,850).

PREPARATIVE EXAMPLES

EXAMPLE 1

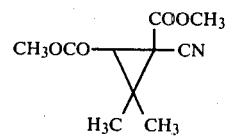

27.2 g (0.1 mol) of $\alpha,\beta$-dibromo-isovaleric acid methyl ester were added dropwise to a solution of 19.9 g (0.2 mol) of cyanoacetic acid methyl ester and 10.8 g (0.2 mol) of sodium methylate in 50 ml of methanol at 20° C. The mixture was then heated to 64° C. for 5 hours. The solvent was then stripped off in vacuo. 100 ml of water and 100 ml of ether were added to the residue. The ether phase was separated off, dried over sodium sulphate and evaporated. The residue was fractionated twice. 12 g (57% of theory) of 3,3-dimethyl-1-cyano-cyclopropane-1,2-dicarboxylic acid dimethyl ester were obtained in the form of a colorless oil of boiling point 152° C./10 mm Hg.

EXAMPLE 2

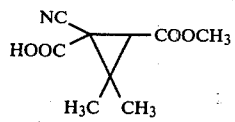

A solution of 21.1 g (0.1 mol) of 3,3-dimethyl-1-cyano-cyclopropane-1,2-dicarboxylic acid dimethyl ester and 5.6 g of potassium hydroxide in a mixture of 50 ml of methanol and 25 ml of water was stirred at room temperature for 2 hours. The mixture was then filtered and the filtrate was acidified with dilute hydrochloric acid. An oil separated out and was taken up in methylene chloride. The methylene chloride phase was dried over sodium sulphate and then concentrated. 13 g (65% of theory) of 3,3-dimethyl-2-methoxycarbonyl-1-cyano-cyclopropane-1-carboxylic acid were obtained in the form of a partly crystalline mass, which could be further processed directly, without purification.

EXAMPLE 3

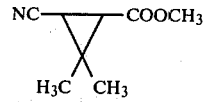

19.7 g (0.1 mol) of the product obtained according to Example 2 were heated to 140°-150° C. in 80 ml of dimethylformamide for 4 hours.

The reaction mixture was then cooled and poured into 200 ml of water. It was subsequently extracted twice with 50 ml of methylene chloride each time. The combined methylene chloride extracts were dried over sodium sulphate and then concentrated. After fractionation, 16 g (75% of theory) of 3,3-dimethyl-2-cyano-cyclopropane-1-carboxylic acid methyl ester were obtained in the form of a colorless oil of boiling point 90°-104° C./2 mm Hg.

EXAMPLE 4

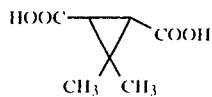

A mixture of 50 ml of 15 percent strength sodium hydroxide solution and 8.5 g (0.05 mol) of 3,3-dimethyl-2-cyano-cyclopropane-1-carboxylic acid methyl ester was boiled under reflux for 18 hours. The mixture was then cooled to 10° C., concentrated hydrochloric acid was added until the pH value had reached about 2 and the mixture was then cooled in an ice-bath for 1 hour. The product which had precipitated was filtered off and rinsed with icewater. 7.3 g (92% of theory) of trans-3,3-dimethylcyclopropane-1,2-dicarboxylic acid were thus obtained in the form of a colorless powder with a melting point of 217° C.

EXAMPLE 5

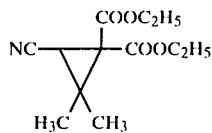

A solution of 24.1 g (0.1 mol) of $\alpha,\beta$-dibromo-isovaleric acid nitrile in 20 ml of dimethylformamide was added dropwise to a mixture of 35 g (0.1 mol) of malonic acid diethyl ester, 30 g of potassium carbonate and 120 ml of dimethylformamide. The internal temperature rose from an initial temperature of about 25° C. to about 40° C. in the exothermic reaction which proceeded during this addition. The reaction mixture was stirred at 20° C. for 15 hours and taken up in 200 ml of toluene and the toluene phase was washed twice with 200 ml of water each time, dried and distilled. A first distillation gave 13.1 g (55% of theory) of 3,3-dimethyl-2-cyano-cyclopropane-1,1-dicarboxylic acid diethyl ester as a product which was 75% pure, according to analysis by gas chromatography, and had a boiling point of 100°–140° C./2 mbar.

A second distillation gave 9.7 g (41% of theory) of pure product.

EXAMPLE 6

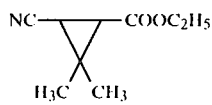

A mixture of 71.7 g (0.3 mol) of 3,3-dimethyl-2-cyano-cyclopropane-1,1-dicarboxylic acid diethyl ester, 6 ml of water and 100 ml of dimethylformamide was heated to the boiling point under reflux for 20 hours. For working up, the mixture was diluted with toluene, washed twice with 300 ml of water each time, dried and distilled. 30.6 g (61% of theory) of 3,3-dimethyl-2-cyano-cyclopropane-1-carboxylic acid ethyl ester of boiling point 87°–95° C./2 mbar were obtained.

EXAMPLE 7

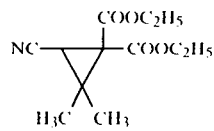

19.2 g of $\alpha$-bromo-$\beta,\beta$-dimethyl-acrylic acid nitrile were added dropwise to a mixture of 20 g of malonic acid diethyl ester, 35 g of potassium carbonate and 80 ml of dimethylformamide. The internal temperature rose from 25° to 30° C. in the exothermic reaction which proceeded during this addition. The reaction mixture was stirred at 20° C. for 15 hours and taken up in methylene chloride and the methylene chloride phase was washed with water, dried and distilled several times.

4.1 g (14% of theory) of 3,3-dimethyl-2-cyano-1,1-dicarboxylic acid diethyl ester with a boiling point of 115°–125° C./2 mbar were obtained.

EXAMPLE 8

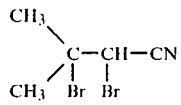

32 g (0.2 mol) of bromine were added dropwise to a solution of 16.2 g (0.2 mol) of $\beta,\beta$-dimethyl-acrylic acid nitrile in 100 ml of carbon tetrachloride. The internal temperature rose from 25° to 35° C. in the exothermic reaction which proceeded during this addition. After stirring the mixture for two hours, it was distilled. 41 g (85% of theory) of $\alpha,\beta$-dibromo-iso-valeric acid nitrile of boiling point 70° C./2 mbar were obtained.

EXAMPLE 9

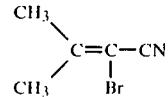

A solution of 101 g (0.42 mol) of $\alpha,\beta$-dibromo-isovaleric acid nitrile in 80 ml of dimethylformamide was added dropwise to a mixture of 63 g of potassium carbonate and 210 ml of dimethylformamide. The internal temperature rose from 20° to 35° C. in the exothermic reaction which proceeded during this addition. The reaction mixture was stirred at room temperature for one hour, diluted with 300 ml of ether and washed twice with 300 ml of water each time. After drying the organic phase with sodium sulphate and subjecting it to fractional distillation, 49.8 g (74% of theory) of $\alpha$-bromo-$\beta,\beta$-dimethyl-acrylic acid nitrile of boiling point 57° C./15 mbar were obtained.

It will be appreciated that the instant specification and examples are set forth by way of illustration and not limitation, and that various modifications and changes may be made without departing from the spirit and scope of the present invention.

We claim:

1. A process for the preparation of a 3,3-dimethyl-cyclopropane-1,1,2-tricarboxylic acid derivative of the formula

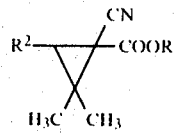

in which
 R is $C_{1-4}$-alkyl, and
 $R^2$ is $C_{1-4}$-alkoxycarbonyl or cyano,
comprising reacting an α-halogenocarboxylic acid derivative of the formula

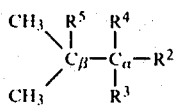

in which
 $R^3$ is bromine or chlorine,
 $R^4$ is hydrogen, and
 $R^5$ is bromine or chlorine, or
 $R^4$ together with $R^5$ constitutes an additional bond between $C_\alpha$ and $C_\beta$,
in liquid phase with a cyanoacetic acid ester of the formula

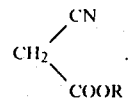

2. A process according to claim 1, wherein the reaction is effected in a polar organic solvent.

3. A process according to claim 1, wherein the reaction is effected in the presence of an alkali metal carbonate, an alkali metal alcoholate or an aliphatic, aromatic or heterocyclic amine.

4. A process according to claim 1, wherein the reaction is effected at about 10° to 80° C.

5. A process according to claim 1, wherein about 1 to 3 mols of the cyanoacetic acid ester are employed per mol of the α-halogenocarboxylic acid derivative.

6. A process according to claim 1, wherein about 1 to 2 mols of the cyanoacetic acid ester are employed per mol of the α-halogenocarboxylic acid derivative.

7. A process according to claim 1, in which the reaction is effected in a polar organic solvent in the presence of an alkali metal carbonate, an alkali metal alcoholate or an aliphatic, aromatic or heterocyclic amine at about 10° to 80° C., and about 1 to 2 mols of the cyanoacetic acid ester are employed per mol of the α-halogenocarboxylic acid derivative.

* * * * *